United States Patent
Thomas et al.

(10) Patent No.: US 7,141,423 B2
(45) Date of Patent: Nov. 28, 2006

(54) CONSTITUTIVE PROMOTER FROM ARABIDOPSIS

(75) Inventors: Terry Thomas, College Station, TX (US); Tzung-Fu Hsieh, Burlingame, CA (US)

(73) Assignee: Biogemma S.A.S., Paris (FR)

( * ) Notice: Subject to any disclaimer, the term of this patent is extended or adjusted under 35 U.S.C. 154(b) by 328 days.

(21) Appl. No.: 10/362,135

(22) PCT Filed: Aug. 21, 2001

(86) PCT No.: PCT/EP01/10982

§ 371 (c)(1),
(2), (4) Date: Aug. 18, 2003

(87) PCT Pub. No.: WO02/16621

PCT Pub. Date: Feb. 28, 2002

(65) Prior Publication Data

US 2004/0029282 A1  Feb. 12, 2004

(51) Int. Cl.
*C12N 15/82* (2006.01)
*A01H 5/00* (2006.01)

(52) U.S. Cl. .................... 435/419; 435/320.1; 800/298

(58) Field of Classification Search ............... 536/24.1; 435/320.1, 419; 800/298
See application file for complete search history.

(56) References Cited

OTHER PUBLICATIONS

Kim Y. et al. A 20 nucleotide upstream element is essential for the nopaline synthase (nos) promoter activity. Plant Mol Biol. Jan. 1994;24(1):105-17.*
Kaneko T. et al. Database EMBL Online, Mar. 6, 2000, Arabidopsis thaliana genomic DNA, chromosome 3, BAC clone:F5N5, database accession No. AP001300.*
Thomas T. et al. May 30, 2002, Arabidopsis ATP sulfurase gene (APS1) promoter, Geneseq accession No. ABA92165.*
Database EMBL 'Onlinel; Mar. 6, 2000; Kaneko, T., et al.; "Arabidopsis thaliana genomic DNA, chromosome 3, BAC clone: F5N5;" database accession No. AP001300; XP002220435; Sequence: nts 21725-24780.
Leustek, T., Murillo M., Cervantes M.: "Cloning of a cDNA encoding ATP Sulfurylase from Arabidopsis thaliana by functional expression in *Saccharomyces cervisiae*;" Plant Physiology; vol. 105, 1994, pp. 897-902; XP002220434.

* cited by examiner

*Primary Examiner*—Cynthia Collins
(74) *Attorney, Agent, or Firm*—Connolly Bove Lodge & Hutz LLP

(57) ABSTRACT

The present invention is directed to a promoter derived from an *Arabidopsis* ATP sulfurase gene. Nucleic acid constructs, vectors, plant cells and transgenic plants comprising the promoter are also provided.

4 Claims, 3 Drawing Sheets

SEQUENCE LISTING

<160> NUMBER OF SEQ ID NOS: 1

<210> SEQ ID NO 1
<211> LENGTH: 3057
<212> TYPE: DNA
<213> ORGANISM: Arabidopsis thaliana
<220> FEATURE:
<221> NAME/KEY: promoter
<222> LOCATION: (7)..(3054)
<223> OTHER INFORMATION: CT1 promoter fragment
<220> FEATURE:
<221> NAME/KEY: primer_bind
<222> LOCATION: (3038)..(3054)
<223> OTHER INFORMATION: Binding site for PCR primer

<400> SEQUENCE: 1

```
aagcttttaa gttttaaagc aagagactat attaaggatc atcgtaagat ttagcaaagt     60
ctaacccaaa aaatacatta agggaaattt ttcagcttaa tatcaaccaa tttagagatt    120
tctaaaaaag aaaattaaaa cttttttttag agatttatat ttttaaaaga gatataaaat    180
tgcctacaga aaatcttcaa ataagccaaa ccagctcagt ttatgaatca ttaaaatgaa    240
acttccttac caatataatt tcaaacgaaa aaaaaattcc gtatcgaatt tttttgtaaa    300
gaaactcatt ttagtgggtt tttataagct agactgatga atttggtcga agtacagctt    360
attggcatct aactcattaa atgcaaatat catacaaaat tcgtaattac atgtaaattt    420
cttccaaaat tcgtaattac atgtatgtaa taatctaatt ttgtgtgtgt tagtgatatt    480
agaaatatta ttgaaaaaat aatataggca tcgtgtgcaa ttttcaatta ccttcacaaa    540
tgaagaaaca ttccgagcat atctccttgg cataatgagt gggatttttag agttaagcca    600
acgaaatttg ggcctaattt ttcatcaaat acttgggcct agtcatcggt tatgtcattg    660
ctacttatat aagacccata ggtataccga taaagtcttc atattgagat ccaaaggccg    720
ggatcgaaca agttttgttc ttattgaatc agcgttagac gcagccttgt ctttattatg    780
ttcttcttca tccgttagaa aaagtatccg tatgatgtcc attcgtttca tttgtaataa    840
tttgatgaag tcttcttaaa gacatttgga ttggagttag aatgttcctt cttttatttt    900
tcttcaggac acttggagtc tcggattagt caagagactt cgatcatatt ttctttatca    960
cctcttcttc aatttatatg gatcatcttt aggaaaacta taacgtgtta attgtgaaat   1020
tatgatacaa actttataat tcataaataa atatgtctgt gcatagtttt tttttttaaa   1080
ttatccggat aatgattatg agagaaaagc aggtaggtcg atcatgaatg tttaattttg   1140
gcacatgttg aatgtgaggt cccagccacc aataaactga tcaagtccta cattatccaa   1200
ttcctttaat taccttaaag tatttacaaa atttgaatta gtcaaatctt tgagttaaga   1260
caccaaatga ttttacaaaa ctcgaataat ataagaagag tatacttgtt gtaaccttgg   1320
agtactacga attcaacaat ttgatgaagt gaaaacatag ttaagaaatg attgggagat   1380
tattcatcta aagctaccag tctaccaact ttccagtttt gacaatattt accacgtggc   1440
cctgaggaac atcattgtca gtttatcaaa cactccatat ttcgtggcag cttcgggtca   1500
agaatccaaa ttggtattgt cacttggtca ggtcaaagtt gaggagcttt tatatatagt   1560
ataatcaatg agtcggctaa aatgtaaaat acatgttcta aattaaacgt aataaattac   1620
tataatcgta tcaaatttat ccctcttatc aaattagtac tttcgagttt cgatattgtt   1680
tctttctctg ggaaactata tatatttaca tttctagaaa gaagaaaaa aactatattt    1740
attacatttt atacgtgcta agcctagaaa agattaatta caaagaaatt atacatttta   1800
```

```
ttgatcaagt ggtgcttaaa gcagtaaaaa caatttgaac tcataaatcg taaatacgtc    1860
gacatatttc gtgatctcca ttaattttc ttttttaaa gattgacgca aaataatatt    1920
ctgaaaatga aaaagtaaaa taagagggga caaatattcg agatgtgacg tggcagatcg    1980
agtggtttaa atattctatt agcaagtggt ttgtgtaata agcaaatggg tggtcgaacc    2040
tgaccgtatt cttggatcta ttcaactgta gcatcagtcc accttcctta cctcatcttt    2100
cctaactttt taataccttt ttaatttgct aaaaacatca ctactattta tatttgatct    2160
ctaattactg tttcaactct gaatattccg taatccttat attaatatgt ccaaaaatat    2220
ataatttctg gactttccct tgagatggga atatgaaaga attgcatcat ttacctaatc    2280
atatgaacac aaatagatat tggaaaaaat gtggttttat ttttcatgtt ttgttcgatt    2340
atctttatct ttatcccaaa aaaaaaaaaa atcattcgat tatatctaaa attcaaaata    2400
tcattagtaa gaatatataa gaatgtaatt agtggaaata catagtaagt atcattggtt    2460
tcattagtaa gaatatataa gaatgtaatt agtggaaata catagtaagt atcattggtt    2520
tttgccacat atggtgagca attttttatt ttaagaaggg aaaatcaatt tgtacataga    2580
tttatgtcac ttattcaatt gaataataca gaaggattta aagtctaaag taaaaacagg    2640
caaaataata atatgttttt ttctttgatc gctcagatta tcgtattaaa atttggatta    2700
tgacataaca acgataataa tacaaactag ttggttatga actctgaata aattattta    2760 aagaaagaat actactattt aattataaaa tgactctgca tcatatcaat aaggtaacct    2820
cgttattata aacgtcacac tacacactat tagtatttta attacacagt gaaaaattt    2880 aattaattac taatctctgt ccaggtacat aatattattc caagatacgg tccttcgtta    2940
ctataaactc tataaaaaac caattttcac ttccaattga attgggaaca aaccaaatct    3000
ctatctctct ccattagagc ttgaagcagc catagcctaa caaaaccttc aacaatg      3057
```

CONSTITUTIVE PROMOTER FROM ARABIDOPSIS

FIELD OF THE INVENTION

The present invention is directed to a promoter derived from an *Arabidopsis* ATP sulfarase gene. The promoter of the invention is useful in transgenic organisms in which a high level of production of a gene product is desired.

BACKGROUND OF THE INVENTION

Promoters are regulatory elements that direct the expression of genes. Both constitutive and regulated promoters are used to direct gene expression in transgenic organisms including plants. Constitutive promoters direct expression in most or all tissues, and are useful when high levels of production of a gene product are desired. The 35S promoter from cauliflower mosaic virus (CMV) is frequently used to direct constitutive expression. Regulated promoters, such as tissue-specific and inducible promoters, are used to direct spatially or temporally specific expression, or expression in response to environmental factors.

The present invention is directed to a promoter that directs constitutive expression of genes in plants. The present promoter is derived from an ATP sulfurase gene of *Arabidopsis thaliana*.

ATP sulfurase catalyzes the formation of adenosine-5'-phosphosulfate from ATP and sulfate in the sulfate assimilation pathway. In *Arabidopsis*, ATP sulfurase is encoded by a gene family of at least three genes, APS1, APS2 and APS3. Leustek et al. (1994) Plant Physiol. 105:897; Murillo et al. (1995) Arch. Biochem. Biophys. 323:195; Klonus et al. (1995) Plant Physiol. 107:653; Logan et al. (1996) J. Biol. Chem. 271:12227. APS1, APS2 and APS3 cDNAs have been isolated and sequenced. Leustek et al. (1994); Murillo et al. (1995).

In accordance with the present invention, it has been discovered that a promoter derived from APS1 can direct high levels of constitutive expression of heterologous genes in plants.

SUMMARY OF THE INVENTION

The present invention is died to an isolated promoter derived from an ATP sulfurase gene of *Arabidopsis thaliana*. In a preferred embodiment the ATP sulfurase gene is the APS1 gene. In another preferred embodiment, the promoter has at least 70% identity to the sequence of SEQ ID NO:1.

The present invention further provides a nucleic acid construct comprising the promoter of the invention operably linked to a heterologous nucleic acid. Vectors comprising the nucleic acid construct are also provided.

In another embodiment, the present invention is directed to a plant cell comprising the nucleic acid construct of the invention. Transgenic plants and progeny thereof comprising the construct, parts of such plants, and methods of making such plants, are also provided.

DETAILED DESCRIPTION OF THE INVENTION

Figure 1:
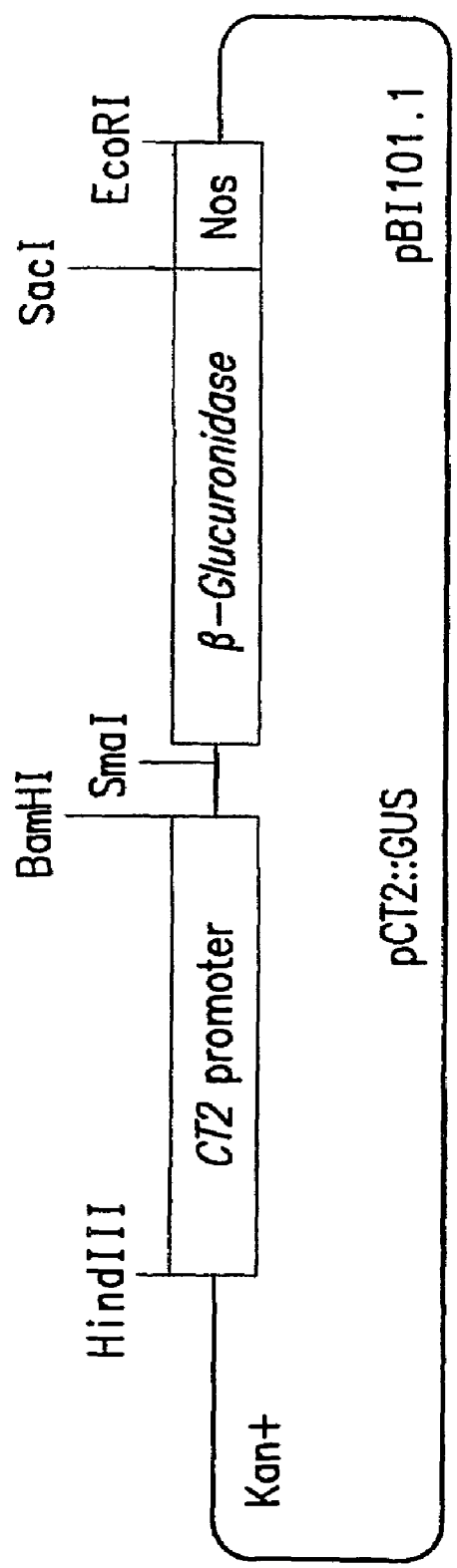
FIG. 1 depicts plasmid pCT2::GUS.

The present invention is directed to a promoter that directs expression of genes in plants. The promoter is derived from an ATP sulfurase gene of *Arabidopsis*. *Arabidopsis* ATP sulfurase genes have been described in the art as APS1, APS2 and APS3. The cDNA encoding APS1 has been described by Leustek et al. (1994) Plant Physiol. 105:897. In accordance with the present invention, the promoter is derived from the APS1 gene and is designated the APS1 promoter.

In a preferred embodiment, the APS1 promoter has the sequence of SEQ ID NO:1, or a fragment thereof that has promoter activity, i.e., drives the expression of a heterologous nucleic acid operably linked thereto. In another preferred embodiment, the APS1 promoter has a sequence that has at least 70% identity to the sequence of SEQ ID NO:1 or a fragment thereof that has promoter activity. More preferably, the APS1 promoter has a sequence that has at least 80%, or more preferably at least 90%, identity to the sequence of SEQ ID NO:1 or a fragment thereof that has promoter activity. Sequence identity as defined herein is measured using the program Clustal W described by Higgins et al. (1994) Nucleic Acids Research 22:4673 and may be calculated using the EMBL Nucleotide Sequence Database (which can be found at the EBI website).

In another embodiment, the APS1 promoter has a nucleic acid sequence that hybridizes to the sequence of SEQ ID NO:1 under high stringency conditions and that has romoter activity. High stringency conditions are defined herein as 68° C. in buffered queous solution or 42° C. in 50% formanide.

The promoters of the present invention may be isolated by using a nucleic acid having the sequence of SEQ ID NO:1 or a fragment thereof to probe a genomic plant library. In addition, APS1 cDNA may be used to probe a genomic plant library. APS1 cDNA is disclosed by Leustek et al. (1994) Plant Physiol. 105:897.

In a preferred embodiment, the library is an *Arabidopsis* genomic library. Such libraries may be made by well-known methods disclosed for example in Sambrook et al. (1989) Molecular Cloning: A Laboratory Manual, 2$^{nd}$ Editon, Cold Spring Harbor Laboratory Press, Cold Spring Harbor, N.Y. The probes can be used to isolate nucleic acids that hybridize to SEQ ID NO:1 under high stringency conditions. High stringency conditions are described in Sambrook et al., id., and Beltz et al. (1983) Methods Enzymol. 100:226 and include, for example, hybridization at 68° C. in aqueous buffered solution or at 42° C. in 50% formamide. Having identified a genomic clone, the promoter can be derived by endonuclease or exonuclease digestion, or PCR amplification.

Further, probes derived from SEQ ID NO:1 or APS1 cDNA may be used to isolate promoters having at least 70%, or at least 80%, or at least 90% identity to SEQ ID NO:1. In addition, well-known methods of enzymatic and chemical modification of nucleic acids may be used to obtain promoters having the stated levels of identity to SEQ ID NO:1 or fragments thereof.

The present invention also encompasses fragments of SEQ ID NO:1 and sequences having at least 70%, or at least 80%, or at least 90% identity thereto that have promoter activity. Those of ordinary skill in the art can determine the sequence required to maintain promoter activity, for example by generating deletion fragments of SEQ ID NO:1 to obtain putative promoters, operably fusing the putative promoter to a transgene, introducing the construct into a host cell, and measuring expression of the transgene. The transgene may be a reporter, for example, the chloramphenicol acetyl transferase (cat), beta-glucuronidase (gus) or luciferase (luc) genes. The construct containing the promoter and transgene is cloned into a vector, and the vector is used to transform host cells. Expression of the transgene is measured by assaying for the transgene product. Standard assays are available to sensitively detect the reporter gene product For example, GUS can be measured by histochemical or fluorogenic assays. Jefferson et al. (1987) EMBO J. 6:3901. The presence of the transgene product is indicative of a functional promoter.

The present invention further provides a nucleic acid construct comprising the promoter operably linked to a heterologous nucleic acid. The heterologous nucleic acid is any nucleic acid other than the APS1 gene. As used herein, the term heterologous nucleic acid includes all synthetically engineered and biologically derived genes which may be introduced into a plant by genetic engineering, including but not limited to nonplant genes, plant genes, modified genes, synthetic genes and portion of genes. The heterologous nucleic acid preferably contains the coding region of a protein or polypeptide or antisense molecule of interest.

Suitable heterologous nucleic acids for use herein include all nucleic acids that will provide or enhance a beneficial feature of the resultant transgenic plant. For example, the nucleic acid may encode proteins or antisense RNA transcripts in order to promote increased food values, higher yields, pest resistance, disease resistance, herbicide tolerance, and the like. Representative nucleic acids include, for example, a bacterial dap A gene for increased lysine; genes that encode *Bacillus thuringiensis* (Bt)endotoxins (inter alia U.S. Pat. Nos. 5,460,963; 5,683,691; 5,545,565; 5,530,197; 5,317,096) or insecticidal toxins isolated from *Photorhabdus* (WO97/17432 or WO98/08932) for insect resistance; lytic peptides genes for disease resistance, genes imparting tolerance to oxynil herbicides (U.S. Pat. Nos. 4,810,648 and 5,559,024), bacterial or plant EPSPS for resistance to glyphosate and EPSPS inhibitor herbicides (U.S. Pat. Nos. 4,940,835, 5,188,642, 4,971,908, 5,145,783, 5,312,910, 5,633,435, 5,627,061, 5,310,667, WO 97/04103); genes imparting tolerance to glufosinate (EP 242 236), bacterial or plant HPPD (WO 96/38567, WO 98/02562) for resistance to HPPD-inhibitor herbicides (i.e. diketones, isoxazoles, etc.), chitase or glucan endo 1, 3-B-glucosidase for fungicidal properties. Also, the nucleic acid may be introduced to act as a genetic tool to generate mutants and/or assist in the identification, genetic tagging, or isolation of segments of monocot genes.

As a preferred embodiment of the present invention, the heterologous nucleic acid encodes a protein to impart herbicide tolerance, more preferably tolerance to an oxynil herbicide (disclosed in U.S. Pat. Nos. 4,810,648 and 5,559,024), to EPSPS inhibitor herbicides, including glyphosate and its various salts (disclosed in U.S. Pat. Nos. 4,535,060; 4,769,061; 5,094,945; 4,940,835; 5,188,642; 4,971,908; 5,145,783; 5,312,910; 5,310,667; 5,633,435; 5,627,061; 5,554,798; 5,633,448; WO 97/04103), to glufosinate (EP 242 236), or to HPPD inhibitors (WO 96/38567 and WO 98/02562). More preferably, the heterologous nucleic acid encodes a protein to impart tolerance to EPSPS inhibitor herbicides.

As another preferred embodiment of the present invention, the heterologous nucleic acid encodes a protein to impart insect resistance, more preferably genes which encode for *Bacillus thuringiensis* (Bt) endotoxins (inter a, U.S. Pat. Nos. 5,460,963; 5,683,691; 5,545,565; 5,530,197; 5,317,096). The nucleic acids that are preferably embraced by the instant invention are cryI, cryII, cryIII, and cryIV genes. More preferably, the genes include: cry1A(a), cryIA (b); cryIA(c); and cryIIIA(a). Most preferably the gene is cryIA(a), cryIA(b) or cryM(c).

The nucleic acid construct comprising the promoter operably linked to a heterologous nucleic acid may be constructed by methods well-known in the art. The term "operably linked" as used herein means that the promoter and heterologous nucleic acid are oriented such that the promoter directs expression of the heterologous nucleic acid, generally in the 5'- to 3'-direction. The constructs may also contain polyadenylation sites at the 3'-end of the heterologous gene.

In another embodiment, the present invention provides vectors comprising the nucleic acid constructs. The vectors may be derived from plasmids, cosmids, bacteriophage and viruses. The vectors include direct DNA delivery vectors, and vectors for *Agrobacterium*-mediated gene transfer. Direct DNA delivery vectors and *Agrobacterium* based vectors, and methods for their construction, are well-known in the art and disclosed for example in "Gene Transfer to Plants", Potrykus et al., eds., Springer-Verlag, Berlin 1995 and "Plant Molecular Biology: A Practical Approach", Shaw, ed., IRL Press, Oxford 1988. Vectors for direct DNA delivery generally contain the nucleic acid construct of the invention in a selectable bacterial replicon, and may further contain additional regulatory elements, reporter genes, and selectable markers. Vectors for *Agrobacterium*-mediated gene transfer generally contain functions to allow maintenance in *E. coli* and *Agrobacterium*, transfer from *E coli* to *Agrobacterium*, and *Agrobacterium* T-DNA border fragments. The vectors may be integrative or binary vectors. The vectors may further contain selectable markers and reporter genes to facilitate identification and selection of transformed cells, and suitable regulatory sequences to enable expression in plants. Weising et al. (1988) Annual Rev. Genetics 22:241 describe components that may be included in the subject vectors such as polyadenylation sequences, marker genes, reporter genes, enhancers, and introns. The present vectors will generally contain either a selectable marker or a reporter gene or both to facilitate identification and selection of transformed cells. Alternatively, the selectable marker may be carried on a separate vector and used in a co-transformation procedure. Both selectable markers and reporter genes may be flanked with appropriate regulatory sequences to enable expression in plants. Useful selectable markers are well known in the art and include, for example, antibiotic and herbicide resistance genes. Specific examples of such genes are disclosed in Weising et al., supra. A preferred selectable marker gene is the hygromycin B phosphotransferase (hpt) coding sequence, which may be derived from *E. coli*. Other selectable markers known in the art include aminoglycoside phosphotransferase gene of transposon Tn5 (AphII) which encodes resistance to the antibiotics kanamycin, neomycin, and G418, as well as those genes which code for resistance or tolerance to glyphosate, bialaphos, methotrexate, imidazolinones, sulfonylureas, bromoxynil, dalapon, and the like. Selectable marker genes that confer herbicide tolerance are also of commercial utility in the resulting transformed plants.

Reporter genes which encode easily assayable marker proteins are well known in the art. In general, a reporter gene is a gene which is not present or expressed by the recipient organism or tissue and which encodes a protein whose expression is manifested by some easily detectable property, e.g. phenotypic change of enzymatic activity. Examples of such genes are provided in Weising et al., supra Preferred genes include the chloramphenicol acetyl transferase (cat) gene from Tn9 of *E. coli*, the beta-gluronidase (gus) gene of the uidA locus of *E. coli*, the green fluorescence protein (GFP) gene from *Aequoria victoria*, and the luciferase (uc) gene from the firefly *Photimus pyralis*.

Other elements such as introns, enhancers, polyadenylation sequences and the like, may also be present in the nucleic acid. These elements must be compatible with the remainder of the gene constructions. Such elements may or may not be necessary for the function of the gene, although they may provide a better expression or functioning of the gene by effecting transcription, stability of the mRNA, or the like. Such elements may be included in the nucleic acid as desired to obtain the optimal performance of the transforming gene in the plant. For example, the maize Adh1S first intron maybe placed between the promoter and the coding sequence of a particular heterologous nucleic acid. This intron, when included in a gene construction, is known to generally increase expression in maize cells of a protein. (Callis et al. (1987) Genes Dev. 1:1183). Other suitable introns include the first intron of the shrunken-1 gene of maize (Maas et al. (1991) Plant Mol. Biol. 16:199); the first intron of the castor bean catalase (cat-1) gene (Ohtaet al. (1990) Plant Cell Physiol. 31:805); potato catalase second intron of the ST-LSI gene (Vancanneytet al. (1990) Mol. Gen. Genet. 220:245); tobacco yellow dwarf virus DSV intron (Morris et al. (1992) Virology 187:633; actin-1 (act-1) intron from rice.(McElroy et al. (1990) Plant Cell 2:163); and triose phosphate isomerase (TPI) intron 1 (Snowden et al. (1996) Plant Mol. Biol. 31:689). However, sufficient expression for a selectable marker to perform satisfactorily can often by obtained without an intron. (Battraw et al. (1990) Plant Mol. Biol. 15:527).

Transcription activators such as enhancers include the tobacco mosaic virus (TMV) translation activator (WO87/07644) and the tobacco etch virus (TEV) translation activator (Carrington et al. (1990) J. Virol. 64:1590). Polyadenylation and terminator regulation sequences include sequences of bacterial origin, such as the nopaline synthase (nos) terminator of *Agrobacterium tumifaciens*, or of plant origin such as the histone terminator (EP 0633317).

The vector comprising the heterologous nucleic acid may also comprise sequences coding for a transit peptide, to drive the protein coded by the heterologous gene into the chromoplasts of the plant cells. Such transit peptides are well known to those of ordinary skill in the art, and may include single transit peptides, as well as multiple transit peptides obtained by the combination of sequences coding for at least two transit peptides. One preferred transit peptide is the Optimized Transit Peptide disclosed in U.S. Pat. No. 5,635, 618, comprising in the direction of transcription a first DNA sequence encoding a first chloroplast transit peptide, a second DNA sequence encoding an N-terminal domain of a mature protein naturally driven into the chromoplasts, and a third DNA sequence encoding a second chloroplast transit peptide.

To determine whether a particular combination of heterologous nucleic acid and recipient plant cells are suitable for use herein, the vector may include a reporter gene. An assay for expression of the reporter gene may then be performed at a suitable time after the heterologous nucleic acid has been introduced into the recipient cells. A preferred such assay entails the use of the *E. coli* beta-glucuronidase (gus) gene described by Jefferson et al. (1987) EMBO J. 6:3901, incorporated herein by reference.

In a preferred embodiment, the vector is a binary vector for *Agrobacterium* mediated gene transfer.

The constructs of the present invention are introduced into plant cells by methods known in the art Direct gene transfer methods include gene transfer to protoplasts by microinjection, electroporation, chemically-induced DNA uptake (Potrykus, supra) and biolistic (microprojectible bombardment) approaches (Klein et al. (1987) Nature 327:70). *Agrobacterium* mediated gene transfer methods include leaf disk transformation, protoplast culture, transformation of seed, stem or root explants, in planta vacuum-infiltration (Potrykus, supra), and transformation of inflorescence (U.S. Pat. No. 6,037,522).

Plant cells into which the nucleic acids of the present invention may be introduced include cells of all plants into which nucleic acids can be transferred. Plant cells include undifferentiated tissues such as calli and differentiated tissues such as embryos, plant portions, plants and seeds. Monocotyledous and dicotyledonous plants are included. In a preferred embodiment the plant is cotton, rice, corn, wheat, barley, oat, rye, oil seed rape, potato, soybean, sunflower, sugar cane, sugar beet, alfalfa, or banana. In a more preferred embodiment, the plant is cotton, corn, or potato, and most preferably cotton.

The promoters, nucleic acid constructs, vectors, and plant cells of the present invention are useful for making recombinant gene products in vitro, and for making transgenic plants with desirable properties.

Another aspect of the invention provides transgenic plants, progeny thereof, and seeds and other parts thereof containing the nucleic acid construct of the present invention. Both monotyledous and dicotyledonous plants are contemplated. Plant cells are transformed with the nucleic acid construct by any of the plant transformation methods described above, and regenerated into a complete transgenic plant by methods well known to those of ordinary skill in the art Potrykus, supra, Shaw, supra). For in planta transformation methods, the regeneration step is not needed. Generally, germinating seeds or wounded plants are inoculated with *Agrobacterium* containing the nucleic acid construct, plants are grown to maturity, and seeds are collected, sown, and transformants are selected.

A method of making a transgenic plant comprising the nucleic acid construct of the present invention comprises transforming a plant cell with a vector comprising the APS1 promoter operably linked to a heterologous gene to provide a transformed plant cell, and regenerating a transgenic plant from the transformed plant cell. Another method of making a transgenic plant comprising the nucleic acid construct of the present invention comprises transforming a seed or immature plant with a vector comprising the APS1 promoter operably linked to a heterologous gene, growing the seed or plant to maturity, obtaining the seeds of the plant, and generating transgenic plants from the seeds. The transgenic plants of the present invention are useful in that they may express a gene product for a desired property such as insect resistance, pesticide resistance, heat, cold or drought tolerance, herbicide tolerance, improved properties, and so on.

The following examples further illustrate the invention.

EXAMPLE 1

An *Arabidopsis* 3-day silique cDNA library was constructed using the lambda ZAPII cDNA library construction kit (Stratagene, LaJolla, Calif.). The cDNA library was converted into plasmid library by mass excision, and bacterial clones were ordered into 384-well microtiter plates. Replica filters were made by gridding four 384-well plates onto a 12 cm×8 cm nylon filter using a Biomek 2000 robot The filter has a 3×3 grid in each well location so that each clone is represented twice. As a result, 1,536 cDNA clones were represented on each nylon filter. Each clone was spotted with an unique duplicate pattern to eliminate false hybridization signals.

Each replica filter was then hybridized with cDNA probes prepared from various *Arabidopsis* tissues or organs. The hybridization results were then scored either manually or by image analysis software to document the hybridization pattern of each clone. The hybridization of each colony to each probe was recorded in a Microsoft Excel database. Sorting algorithms were then utilized to determine the colonies representing putative tissue-specific or constitutive genes. The random-primed PCR technique (RP-PCR) described by Li et al. (1998) Plant Cell 10:383 was used for cDNA probe preparation to increase the detection sensitivity. Four filters were constructed to represent 6,144 anonymous cDNA clones. Seven filter sets were made and hybridized to RP-PCR probes synthesized from *Arabidopsis* root, leaf, stem, whole silique, silique without seeds, seedling, and flower tissues. Seventeen putative constitutive clones were identified and subjected to further characterization. The identity of each clone was determined by DNA sequencing and database searches. RNA dot blot analysis was used to assess the expression pattern of each candidate gene. In order to gain quantitative information on each clone's expression level, RNA dot blot analysis was performed using RNAs isolated from a transgenic *Arabidopsis* line that harbors a 35S:GUS construct (obtained from the Arabidopsis Biological Resource Center (ABRC) at Ohio State University, 1735 Neil Avenue, Columbus, Ohio 43210). Relative transcription activity of each gene was then directly compared with the 35S promoter by incorporating a GUS probe in RNA dot blot analysis.

A clone designated CT2 was among the putative constitutive clones chosen for further characterization based on its high levels of expression revealed by RNA dot blot analysis. RNA gel blot analysis showed that CT2 is expressed in all the tissues examined (stem, leaf, flower, root, silique without seeds, whole silique and seeding) at high levels. Sequence analysis indicated that CT2 encoded an ATP sulfurase, and that CT2 corresponds to the APS1 gene described by Leustek et al. (1994) Plant Physiol. 105:897.

In order to isolate the CT2 promoter, an *Arabidopsis* bacterial artificial chromosome (BAC) genomic library obtained from ABRC was screened to identify the clones that contain the CT2 gene. By screening a set of 3 filters containing 4,608 *Arabidopsis* BAC clones (available from ABRC), 3 BAC clones were identified that hybridized strongly to a CT2 cDNA probe. One of them, T3J23, was obtained from the ABRC and was subsequently shown by restriction mapping to contain the genomic region including CT2 gene. A shotgun cloning strategy was used to subclone a 3.2 kb HindIII fragment into the cloning vector pUC18.

The 3.2 kb genomic HindIII fragment was sequenced and found to contain 200 base pairs of CT2 coding region as well as its promoter sequences. SEQ IN NO:1 shows a 3054 bp fragment that lies immediately upstream of the putative translation start site. A Bam HI site was introduced at the 3' end of the promoter during PCR to facilitate subsequent cloning.

The 3 kb promoter fragment was amplified by PCR. The primer sequence used for amplification is at nucleotides 3038–3054 of SEQ ID NO:1. The amplified fragment was cloned into the plant transformation vector pBI101.1 at the HindIII/Bam HI sites to create a translation fusion with the GUS reporter gene. (pBI 101.1 contains the coding region of GUS ligated 5' of the nopaline synthase polyadenylation site in the polylinker site of pBIN 19 (Bevan (1984) Nucleic Acids Res. 12:8711) which contains restriction sites upstream of the initiation codon of GUS for promoter insection). The resulting plasmid, pCT2::GUS, is shown in FIG. 1.

EXAMPLE 2

Figure 2D:
FIGS. 2A–G show histochemical staining of GUS gene expression driven by the APS1 promoter (A–F) and the 35S promoter (G).
Figure 2C:
Figure 2B:
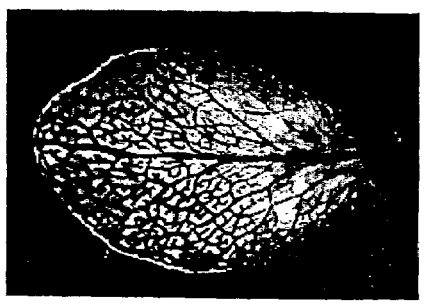
Figure 2A:
Figure 2G:
Figure 2F:
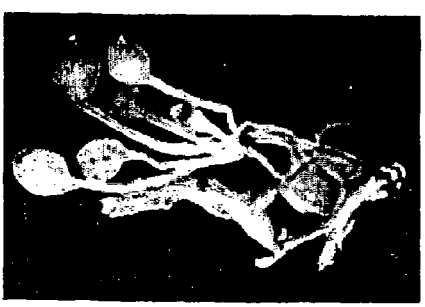
Figure 2E:

The plasmid pCT2::GUS described in Example 1 was used to transform wild type *Arabidopsis* via vacuum filtration as described by Bechtold et al. (1993) Life Sciences 316:1194. Transgenic plants were recovered and assayed for GUS expression according to Jefferson et al. (1987) EMBO J. 6:3901 Histochemical GUS staining analysis showed that the CT2 promoter drives GUS expression in most of the transgenic plant tissues, as depicted in FIG. 2. FIGS. 2A–F show histochemical staining of GUS gene expression driven by the CT2 promoter in cauline leaf (A), rosette leaf (B), inflorescence (C), silique (D), root (E) and seeding (F). FIG. 2G shows GUS gene expression driven by the 35S promoter.

GUS gene expression was found in almost all of the major plant tissues. Further, the CT2 driven GUS gene is expressed throughout the plant life cycle. Thus the CT2 promoter is a constitutive promoter that drives transgene expression in most of the major plant tissues throughout their life cycles.

EXAMPLE 3

Figure 3:
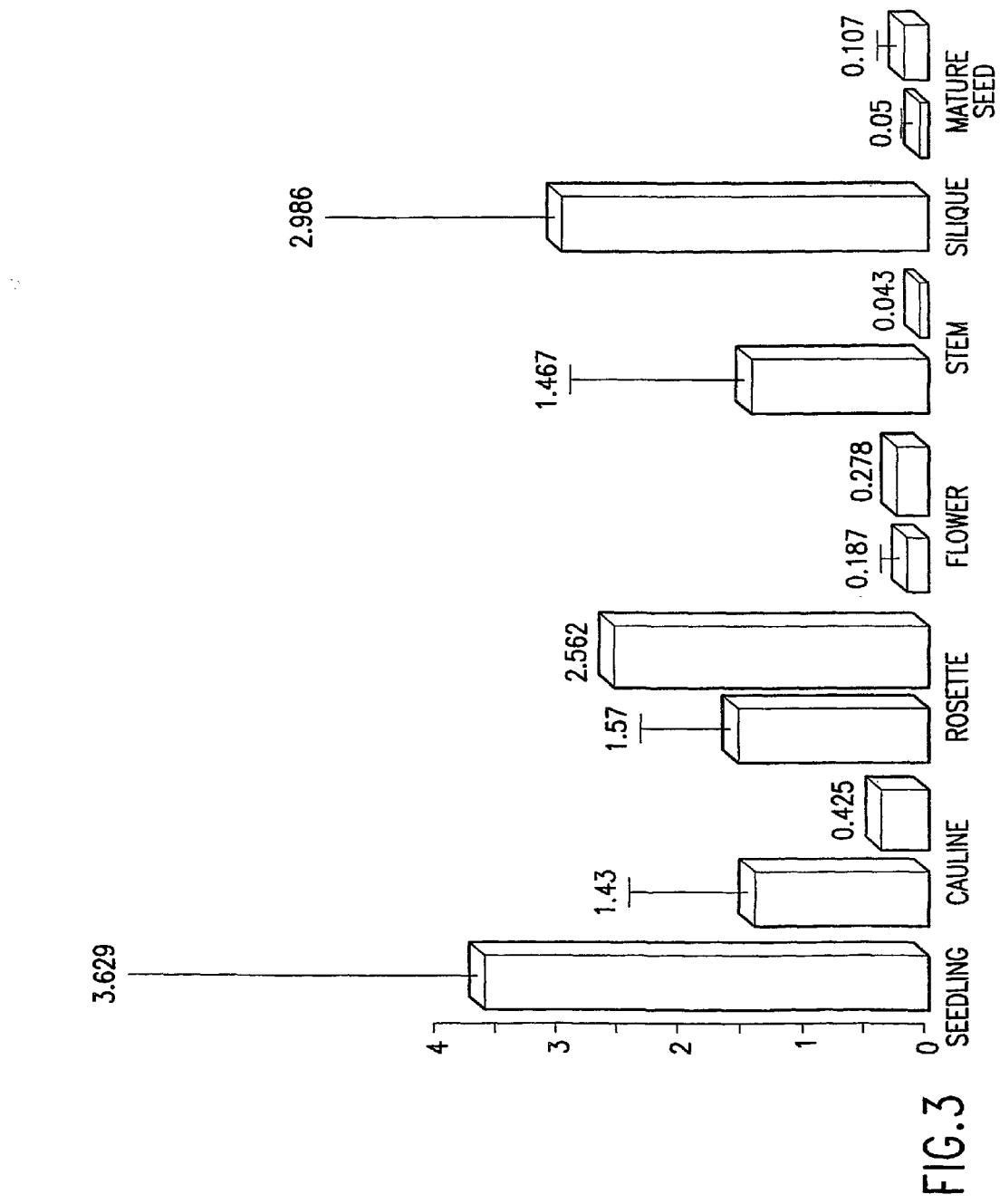
FIG. 3 is a graph comparing relative promoter activity of the 35S and APS1 promoters.

A fluorometric GUS assay was performed to determine the CT2 promoter activity quantitatively according to Jefferson et al., id. Six to eight independent lines were assayed for CT2 promoter activity. FIG. 3 is a graph showing a comparison of relative promoter activity between the 35S and CT2 promoters by fluorometric GUS assays.

As shown in FIG. 3, the activity of the CT2 promoter is comparable to or greater than the 35S promoter. In developing seed, GUS gene expression is relatively low compared to the 35S promoter. Thus the CT2 promoter is ideal for applications in which strong constitutive expression of a transgene is desired in plant tissues except seed. One example is the expression of pesticide resistance genes or insecticidal genes for crop protection, in which expression of such genes in seeds is not desirable.

All references cited herein are incorporated herein in their entirety.

The invention claimed is:

1. A nucleic acid construct comprising an isolated nucleic acid comprising SEQ ID NO: 1, operably linked to a heterologous nucleic acid.

2. A vector comprising the nucleic acid construct of claim 1.

3. A plant cell comprising the nucleic acid construct of claim 1.

4. A transgenic plant or the progeny thereof comprising the nucleic acid construct of claim 1 or the plant cell of claim 3.

* * * * *